(12) United States Patent
Schweizer et al.

(10) Patent No.: US 8,999,942 B2
(45) Date of Patent: *Apr. 7, 2015

(54) POLYOL MODIFIED AMINOGLYCOSIDE-LIPID CONJUGATES

(75) Inventors: Frank Schweizer, Winnipeg (CA); Smritilekha Bera, Dist-West Midnapore (IN); George Zhanel, Winnipeg (CA)

(73) Assignee: University of Manitoba, Winnipeg (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/639,223

(22) PCT Filed: Apr. 5, 2011

(86) PCT No.: PCT/IB2011/001226
§ 371 (c)(1), (2), (4) Date: Feb. 22, 2013

(87) PCT Pub. No.: WO2011/124986
PCT Pub. Date: Oct. 13, 2011

(65) Prior Publication Data
US 2013/0157969 A1 Jun. 20, 2013

Related U.S. Application Data

(60) Provisional application No. 61/321,436, filed on Apr. 6, 2010.

(51) Int. Cl.
| | | |
|---|---|---|
| *A61K 31/7036* | (2006.01) | |
| *A61K 31/7008* | (2006.01) | |
| *A61K 31/702* | (2006.01) | |
| *A61K 31/7028* | (2006.01) | |
| *C07H 15/234* | (2006.01) | |
| *C07H 15/232* | (2006.01) | |
| *C07H 5/06* | (2006.01) | |
| *C07H 15/224* | (2006.01) | |
| *C07H 17/04* | (2006.01) | |

(52) U.S. Cl.
CPC .............. *C07H 15/224* (2013.01); *C07H 17/04* (2013.01)

(58) Field of Classification Search
USPC ................ 514/36, 39, 41, 54; 536/13.2, 13.3, 536/13.6, 13.7, 13.8, 14
See application file for complete search history.

(56) References Cited

U.S. PATENT DOCUMENTS

| | | | | |
|---|---|---|---|---|
| 3,781,268 | A | 12/1973 | Kawaguchi et al. | 536/13.8 |
| 2004/0229265 | A1* | 11/2004 | Lapidot et al. | 435/6 |
| 2006/0234961 | A1 | 10/2006 | Chang | 514/38 |

FOREIGN PATENT DOCUMENTS

| | | |
|---|---|---|
| WO | WO/2007/064954 | 6/2007 |
| WO | WO/2008/092690 | 8/2008 |
| WO | WO-2009/095588 | 6/2009 |
| WO | WO-2010/004433 | 1/2010 |

OTHER PUBLICATIONS

Borodina et al. (Applied and Environmental Microbiology, May 2005, p. 2294-2302).*
Belmont et al. (J Gene Med 2002; 4: 517-526).*
Hichens et al. (Journal of Antibiotics (1973), 26(10), 551-61) (abstract sent).*
Li et al. (Journal of Chinese Pharmaceutical Sciences (2009), 18(4), 302-312) (abstract sent).*
Bera et al., "Antibacterial Activities of Aminoglycoside Antibiotics-Derived Cationic Amphiphiles. Polyol-Modified Neomycin B-, Kanamycin A-, Amikacin-, and Neamine-Based Amphiphiles with Potent Broad Spectrum Antibacterial Activity", J. Med. Chem. Apr. 7, 2010, 53, pp. 3626-3631.
Finley et al., "Cationic Ampiphiles, a New Generation of Antimicrobialinspired by the Natural Antimicrobial Peptide Scafold", Antimicrob. Agents Chemother. Oct. 2010, 54, 4049-4058.
International Preliminary Report on Patentability in PCT Application No. PCT/IB2011/001226, mailed Oct. 18, 2011.
International Search Report and Written Opinion issued in PCT Application No. PCT/IB2011/001226, mailed Sep. 29, 2011.
Kawabe et al., "Acetylation of Amikacin, a new semisynthetic antibiotic, by *Pseudomonas aeruginosa* carrying an R factor", Antimicrob. Agents Chemother. 1975, vol. 7, No. 1, p. 50-54.
Van Schapdael et al., "New Derivatives of Kanamycin B Obtained by Modifications and Substitutions in Position 6". I. Synthesis and Microbiological Evaluation , J. Med. Chem. 1991, 34, 1468-1475.
Zhang et al., "Surprising Alteration of Antibacterial Activity of 5"-Modified Neomycin against Resistant Bacteria", J. Med. Chem. 2008, 51, 7563-7573.
Bera, et al., *J Med Chem*. 51(19):6160-164, 2008.
European Search Report from European Application No. 11765147.1 issued Sep. 24, 2013.
Pathak, et al., *Helvetica Chimica Acta*. 91(8):1533-52, 2008.
Toda, et al., *J Antibiot*. 36(1):87-91, 1983.

* cited by examiner

*Primary Examiner* — Shaojia Anna Jiang
*Assistant Examiner* — Michael C Henry
(74) *Attorney, Agent, or Firm* — Norton Rose Fulbright US LLP

(57) ABSTRACT

In some aspects, the present invention provides aminoglycoside derivatives thereof that exhibit antibacterial activity. In some aspects, the aminoglycoside derivatives comprise compounds consisting of (a) an ammoglycoside group and (b) at least one hydrophobic carbamate and alkoxy group to the primary or secondary hydroxy position of the aminolvcoside group and salts thereof. Additionally, methods of treating and preventing bacterial infections using the aminoglycoside derivatives are also provided.

11 Claims, 2 Drawing Sheets

POLYOL MODIFIED AMINOGLYCOSIDE-LIPID CONJUGATES

CROSS-REFERENCE TO RELATED APPLICATIONS

This application is a national phase application under 35 U.S.C. §371 of International Application No. PCT/IB2011/001226 filed Apr. 5, 2011, which claims priority to U.S. Provisional Application Ser. No. 61/321,436 filed Apr. 6, 2010. The entire contents of each of the above-referenced disclosures are specifically incorporated herein by reference without disclaimer.

BACKGROUND OF THE INVENTION

1. Field of the Invention

The present invention relates generally to the fields of organic chemistry and antibacterial agents. More particularly, it concerns preparation of aminoglycoside derivatives, compositions comprising aminoglycoside derivatives, and methods of treating antibacterial infections with the same.

2. Description of the Related Art

The explosive growth of multidrug-resistant bacteria in hospitals and the community have led to an emerging crisis where an increasing number of antibiotics cease to be of microbiological and clinical usefulness (Boucher et al., 2009; Neu, 1992). As a result, there is a pressing need for novel classes of antibacterial agents with new or combined mechanisms of action that are active against multidrug-resistant bacteria and possess reduced likelihood for the development of resistance. Oligocationic antibacterials (OCAs) containing multiple positively charged amino functions or other cationic groups define a structurally diverse class of antibacterials with broad-spectrum activity and different modes of action (Peterson et al., 1985; Moore et al., 1986; Vaara and Vaara, 1983). This class of antibacterial agents can be further subdivided into non-amphiphilic OCAs such as aminoglycosides (Davis, 1987; Arya, 2007) but also amphiphilic OCAs comprised of the naturally occurring cationic antimicrobial peptides (Hancock and Sahl, 2006; Zasloff, 2002), synthetic mimics of antimicrobial peptides (SMAMPs) (Hamuro et al., 1999; Porter et al., 2000; Schmitt et al., 2007; Patch and Barron, 2004 Radzishevsky et al., 2007; Zorko et al., 2005; Liu et al., 2004; Tew et al., 2002; Chongsiriwatana et al., 2008 Som and Tew, 2008), synthetic oligocationic lipopeptides (Makovitzki et al., 2006; Andrä et al., 2005; Japelj et al., 2007; Majerle et al., 2003 Wakabayashi et al., 1999; Malina and Shai, 2005; Shai et al., 2006), oligocationic lipids (Vieira and Carmona-Ribeiro, 2006; David, 2001; Savage et al., 2002), and polymers (Palermo and Kuroda, 2009). The cationic charges of the OCA ensure accumulation at polyanionic microbial cell surfaces that contain acidic polymers, such as lipopolysaccharides, and wall-associated teichoic acids in Gram-negative and Gram-positive bacteria, respectively (Hancock and Sahl, 2006). Several OCAs including aminoglycoside antibiotics (gentamicin) and antimicrobial peptides (polymyxin B, defensins, gramicidin S variants, and others) transit the outer membrane by interacting at sites at which divalent cations crossbridge adjacent polyanionic polymers. This causes a destabilization of the outer membrane that is proposed to lead to self-promoted uptake of the OCAs and/or other extracellular molecules (Hancock and Sahl, 2006; Hancock and Bell, 1988). After transit through the outer membrane OCAs contact the anionic surface of the cytoplasmic membrane. Here depending on the structure of the OCA several scenarios can be envisaged. Amphiphilic OCAs can insert themselves into the cytoplasmic membrane thereby either disrupting the physical integrity of the bilayer, via membrane thinning, transient poration and/or disruption of the barrier function, or translocate across the membrane and act on internal targets (Hancock and Sahl, 2006). This mode of action has been shown to limit the risk of cross resistance (Hancock and Sahl, 2006; Zasloff, 2002; Chopra et al., 1997) and several amphiphilic OCAs including chlorhexidine and polymyxins are in use as antiseptics, disinfectants and antibiotics for several decades with little or no occurrence of resistance (Gilbert and Moore, 2005; Chen and Kaye, 2009). Non-amphiphilic OCAs such as aminoglycoside antibiotics must cross the bacterial membrane in order to bind to intracellular targets such as RNA, DNA and proteins. In this case co-administration with membrane permeabilizing agents such as ionic lipids can result in synergistic enhancements of the antibacterial action (Shelburne et al., 2004; Drew et al., 2009). It is generally believed that the selective bacterial cytotoxicity of OCAs is caused by the affinity of the net negative charge found on bacterial cell membranes in contrast to eukaryotic lipid bilayers which are typically made up of zwitterionic phospholipids (Hancock and Sahl, 2006).

Aminoglycoside antibiotics constitute a large family of clinically important non-amphiphilic OCAs used in the treatment of bacterial infections (Davis, 1987; Ayra, 2007). Aminoglycosides effect their antibacterial activity by interfering with ribosomal function (via binding to the A-site region on the 16S subunit of rRNA), which ultimately results in the disruption of protein biosynthesis (Moazed and Noller, 1987; Purohit and Stern, 1994). Although aminoglycoside antibiotics exhibit potent bactericidal activity, their widespread use has been compromised by the worldwide emergence and spread of aminoglycoside-resistant strains (Boucher et al., 2009) and toxicity (Giuliano et al., 1984; Tran Ba Huy et al., 1986). Several mechanisms cause resistance including decreased uptake into cells, as a result of activation of drug efflux pumps, modified membrane potential, changes in membrane composition, covalent modification of the drug and others (Magnet, S.; Blanchard, 2005; Taber et al., 1987; Wright et al., 1998; Shakya and Wright, 2007).

As a result, there is a pressing need for novel classes of antibacterial agents with reduced resistance.

SUMMARY OF THE INVENTION

The present invention provides novel aminoglycoside derivatives that exhibit antibacterial activity. Indeed, at least some of the aminoglycoside derivatives discussed herein show marked improvements over traditional aminoglycoside antibiotics, such as neomycin and kanamycin. In addition to providing methods of making aminoglycoside derivatives, methods of treating bacterial infections using these aminoglycoside derivatives are also provided by the present invention.

Accordingly, in some aspects, the present invention provides an aminoglycoside derivative comprising (a) an aminoglycoside group; and (b) at least one carbamate group or alkoxy group (thereby forming an ether group) attached to a primary or secondary hydroxy position of the aminoglycoside group; or a salt thereof.

In any embodiments herein that employs an aminoglycoside, the aminoglycoside may be an aminoglycoside antibiotic. Such agents are well known in the art. In certain embodiments, the aminoglycoside antibiotic is selected from the group consisting of a neomycin, a kanamycin, paromomycin, amikacin, a gentamicin, netilmycin, a streptomycin, tobramycin, a hygromycin and a spectinomycin. In some embodiments, the aminoglycoside antibiotic is selected from the group consisting of a neomycin, kanamycin, amikacin, streptomycin, tobramycin and hygromycin. In more particular embodiments, the aminoglycoside antibiotic is neomycin or kanamycin. Any one or more of these aminoglycoside antibiotics may be excluded, in certain embodiments.

Any aminoglycoside employed herein may exist with one or more free amino groups (—$NH_2$). In such embodiments, the aminoglycoside or aminoglycoside derivative may exist as a trifluoroacetic acid salt (TFA salt).

Non-limiting examples of aminoglycoside derivatives of the present invention include:

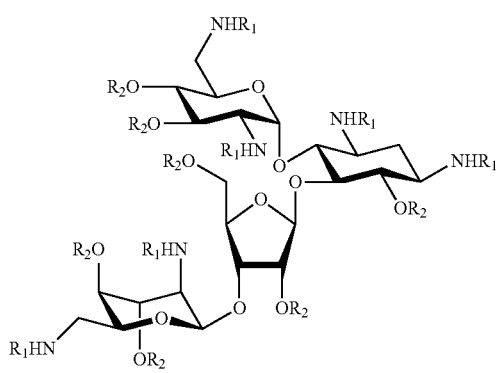

wherein each $R_1$ and each $R_2$ are each independently H, —C(NH)$NH_2$, —C(O)($NH_2$), alkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, or substituted versions thereof, provided that not all $R_1$ and $R_2$ are H; or pharmaceutically-acceptable salts thereof. In some embodiments, $R_1$ is H; and $R_2$ is C(O)NH$C_6H_5$, —C(O)NH-p-$C_6H_4$Cl, —C(O)NH$C_6H_{13}$, —C(O)NH-p-$C_6H_4$N(Me)$_2$, —$CH_2C_6H_5$, —$CH_2$-p-$C_6H_4$Cl, —$CH_2$-p-$C_6H_4$C($CH_3$)$_4$, or $CH_3$. In certain embodiments, $R_2$ is C(O)NH$C_6H_5$. In another embodiment, $R_2$ is $CH_2C_6H_5$.

Other examples of aminoglycoside derivatives of the present invention include:

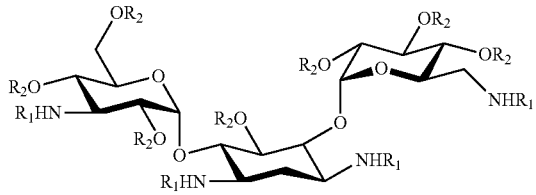

wherein each $R_1$ and each $R_2$ are each independently H, —C(NH)$NH_2$, —C(O)($NH_2$), alkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, or substituted versions thereof, provided that not all $R_1$ and $R_2$ are H; or pharmaceutically-acceptable salts thereof. In some embodiments, $R_1$ is H or C(NH)$NH_2$; and $R_2$ is C(O)NH$C_6H_5$, —C(O)NH$C_6H_{13}$, —C(O)NH-p-$C_6H_4$N(Me)$_2$, $CH_2C_6H_5$, —$CH_2$-p-$C_6H_4$Cl, or $CH_3$.

Still further examples of aminoglycoside derivatives of the present invention include:

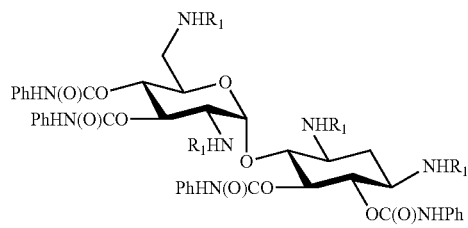

wherein each $R_1$ is H, —C(NH)$NH_2$, —C(O)($NH_2$), alkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, or substituted versions thereof; or pharmaceutically-acceptable salts thereof. In some embodiments, $R_1$ is H.

Still further examples of aminoglycoside derivatives of the present invention include:

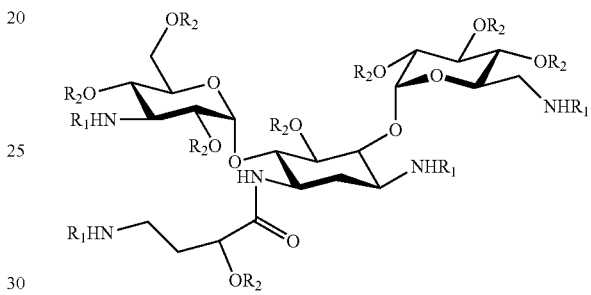

wherein each $R_1$ and each $R_2$ are each independently H, —C(NH)$NH_2$, —C(O)($NH_2$), alkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, acyl$_{(C \leq 18)}$, or substituted versions thereof, provided that not all $R_1$ and $R_2$ are H; or pharmaceutically-acceptable salts thereof. In some embodiments, $R_1$ is H; and $R_2$ is C(O)NH$C_6H_5$, —C(O)NH$C_6H_{13}$, —$CH_2C_6H_5$, —$CH_2$-p-$C_6H_4$Cl, or $CH_3$. In certain embodiments, $R_2$ is C(O)NH$C_6H_{13}$.

The present invention also contemplates pharmaceutical compositions. A pharmaceutical composition may comprise, for example, an aminoglycoside derivative comprising: (a) an aminoglycoside group; and (b) at least one carbamate group or alkoxy group attached to a primary or secondary hydroxy position of the aminoglycoside group; or a salt thereof in a pharmaceutically acceptable formulation. In other embodiments, the aminoglycoside derivative may be any aminoglycoside derivative described herein.

The aminoglycoside derivatives as disclosed herein may be used in methods of treatment. In some aspects, the invention provides a method of treating a bacterial infection in a subject comprising administering to the subject an effective amount of an aminoglycoside derivative comprising: (a) an aminoglycoside group; and (b) at least one carbamate group or alkoxy group attached to a primary or secondary hydroxy position of the aminoglycoside group. In other embodiments, the aminoglycoside derivative may be any aminoglycoside derivative described herein. The bacteria causing the bacterial infection may be a multi-drug resistant bacteria, for example.

The bacterial infection may be caused by, for example, a Gram-positive bacteria. Non-limiting examples of Gram-positive bacteria include *Staphylococcus aureus*, methicillin-resistant *Staphylococcus aureus* (MRSA), *Staphylococcus epidermidis*, methicillin-resistant *S. epidermidis* (MRSE), *Enterococcus faecalis*, *Enterococcus faecium*, or *Streptococcus pneumoniae*.

The bacterial infection may be caused by, for example, a Gram-negative bacteria. Non-limiting examples of Gram-negative bacteria include *E. coli*, gentamicin-resistant *E. coli* or amikacin-resistant *E. coli*, *P. aeruginosa* or gentamicin-resistant *P. aeruginosa*, *Stenotrophomonas maltophilia*, or *Acinetobacter baumanni*.

In certain embodiments regarding treatment of a bacterial infection using a aminoglycoside derivative of the present invention, the minimum inhibitory concentration of the aminoglycoside antibiotic derivative (MIC) is ≤64 μg/mL. In certain embodiments, the MIC is ≤32 μg/mL. In certain embodiments, the minimum inhibitory concentration is about, at most about, or at least about 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or lower μg/mL, or any range derivable therein. Certain methods contemplate an additional step comprising administration of a second antibacterial agent.

In certain embodiments, methods of the present invention may further comprise diagnosing a subject as needing treatment for a bacterial infection prior to administering the aminoglycoside derivative.

Also contemplated are methods of preventing a bacterial infection in a subject comprising administering to the subject an effective amount of an aminoglycoside derivative comprising: (a) an aminoglycoside group; and (b) at least one hydrophobic group attached to a primary or secondary carbon atom of the aminoglycoside group. Such methods may further comprise diagnosing the subject as needing preventative treatment for the bacterial infection prior to administering the aminoglycoside antibiotic derivative.

Embodiments discussed in the context of methods and/or compositions of the invention may be employed with respect to any other method or composition described herein. Thus, an embodiment pertaining to one method or composition may be applied to other methods and compositions of the invention as well.

In some embodiments, "hydrophobic group" refers to a straight-chain hydrocarbon radical having 5 carbons or higher, wherein the radical may comprise single, double, and/or triple bonds or may be cyclic or aromatic. In certain embodiments, the straight-chain hydrocarbon radical has between 5 and 45 carbon atoms. In certain embodiments, the hydrophobic group may comprise only single bonds. In certain embodiments, the hydrophobic group may comprise 20 or fewer double bonds. In certain embodiments, the hydrophobic group may comprise at most or at least 19, 18, 17, 16, 15, 14, 13, 12, 11, 10, 9, 8, 7, 6, 5, 4, 3, 2, or 1 double bond(s), or any range derivable therein. In certain embodiments, the hydrophobic group may comprise 10 or fewer triple bonds. In certain embodiments, the hydrophobic group may comprise at most or at least 9, 8, 7, 6, 5, 4, 3, 2, or 1 triple bond(s), or any range derivable therein. In certain embodiments, the hydrophobic group may be of the formula $C_aH_{2a+1}$, wherein a is 5-45. In certain embodiments, a is at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or higher, or any range derivable therein. In certain embodiments, one or more of the hydrophobic groups is alkyl$_{(C5-45)}$, for example, a straight-chain alkyl$_{(C5-45)}$. In other embodiments, one or more of the hydrocarbon chains is an alkenyl group. Non-limiting examples of hydrophobic groups include —$C_5H_{11}$, —$C_{11}H_{23}$, —$C_{15}H_{31}$, —$C_{19}H_{39}$ and —$C_{17}H_{31}$. An aminoglycoside derivative may comprise more than one hydrophobic group.

As used herein, "conjugation" and "conjugate" refer to covalent bonds between entities, unless specifically noted otherwise.

When used in the context of a chemical group, "hydrogen" means —H; "hydroxy" means OH; "oxo" means =O; "halo" means independently —F, —Cl, —Br or —I; "amino" means —NH$_2$; "hydroxyamino" means NHOH; "nitro" means NO$_2$; imino means =NH; "cyano" means —CN; "azido" means —N$_3$; in a monovalent context "phosphate" means —OP(O)(OH)$_2$ or a deprotonated form thereof; in a divalent context "phosphate" means —OP(O)(OH)O or a deprotonated form thereof; "mercapto" means —SH; "thio" means =S; "thioether" means —S—; "sulfonamido" means —NHS(O)$_2$—; "sulfonyl" means —S(O)$_2$— (see below for definitions of groups containing the term sulfonyl, e.g., alkylsulfonyl); "sulfinyl" means —S(O)—; and "silyl" means —SiH$_3$.

The term "alkoxy" when used without the "substituted" modifier refers to the group OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group OR, in which R is a substituted alkyl, as that term is defined above. For example, —OCH$_2$CF$_3$ is a substituted alkoxy group.

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question, e.g., it is understood that the minimum number of carbon atoms in the group "alkenyl$_{(C≤18)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$—OCH$_3$, —CH$_2$—OCH$_2$CF$_3$, —CH$_2$OC(O)CH$_3$, —CH$_2$—NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

As used herein, "protecting group" refers to a moiety attached to a functional group to prevent an otherwise unwanted reaction of that functional group. The term "functional group" generally refers to how persons of skill in the art classify chemically reactive groups. Examples of functional groups include hydroxyl, amine, sulfhydryl, amide, carboxyl, carbonyl, guanidino, etc. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups, including examples of their installation and removal, may be found in Greene and Wuts, 1999, incorporated herein by reference in its entirety. Triazole aminoglycoside-(amino acid)$_n$ conjugates described herein are contemplated as protected by one or more protecting groups—that is, the present invention contemplates such conjugates in their "protected form." Non-limiting examples of carboxylic acid protecting groups include benzyl (Bn) and t-butyl. Non-limiting examples of amino protecting groups include Bn, carbobenzyloxy (Cbz), t-butoxycarbonyl (Boc) and 9-fluorenylmethyloxycarbonyl (Fmoc), for example.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers.

Synthetic techniques that may be used to prepare certain compounds of the present invention are provided in the Examples section. These techniques may be expanded to produce other aminoglycoside derivatives using techniques known in the art. Other synthetic techniques to prepare compounds of the present invention, such as precursors, as well as derivatives are well-known to those of skill in the art. For example, Smith and March, 2001 discuss a wide variety of synthetic transformations, reaction conditions, and possible pitfalls relating thereto, including amidation and esterification reactions. Methods of oxidizing a primary hydroxy position of an aminoglycoside such that is may be further reacted to produce a aminoglycoside derivative are discussed in, for example, Kudyba et al., 2007, which is incorporated herein by reference in its entirety. Methods discussed therein may be adapted to prepare compounds of the present invention from commerically available starting materials.

As used herein, the term "patient" or "subject" refers to a living mammalian organism, such as a human, monkey, cow, sheep, goat, dogs, cat, mouse, rat, guinea pig, or transgenic species thereof. In certain embodiments, the patient or subject is a primate. Non-limiting examples of human subjects are adults, juveniles, infants and fetuses.

As used herein, a "multidrug resistant (MDR) bacteria" is resistant to two or more antimicrobial classes.

The claimed invention is also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps during synthesis. Salts include, but are not limited to, sodium, lithium, potassium, amines, tartrates, citrates, hydrohalides, phosphates and the like.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Descriptions of well-known processing techniques, components, and equipment are omitted so as not to unnecessarily obscure the present methods and devices in unnecessary detail. Other objects, features and advantages of the present invention will become apparent from the following detailed description. It should be understood, however, that the detailed description and the specific examples, while indicating specific embodiments of the invention, are given by way of illustration only, as various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DESCRIPTION OF THE ILLUSTRATIVE EMBODIMENTS

Figure 1:
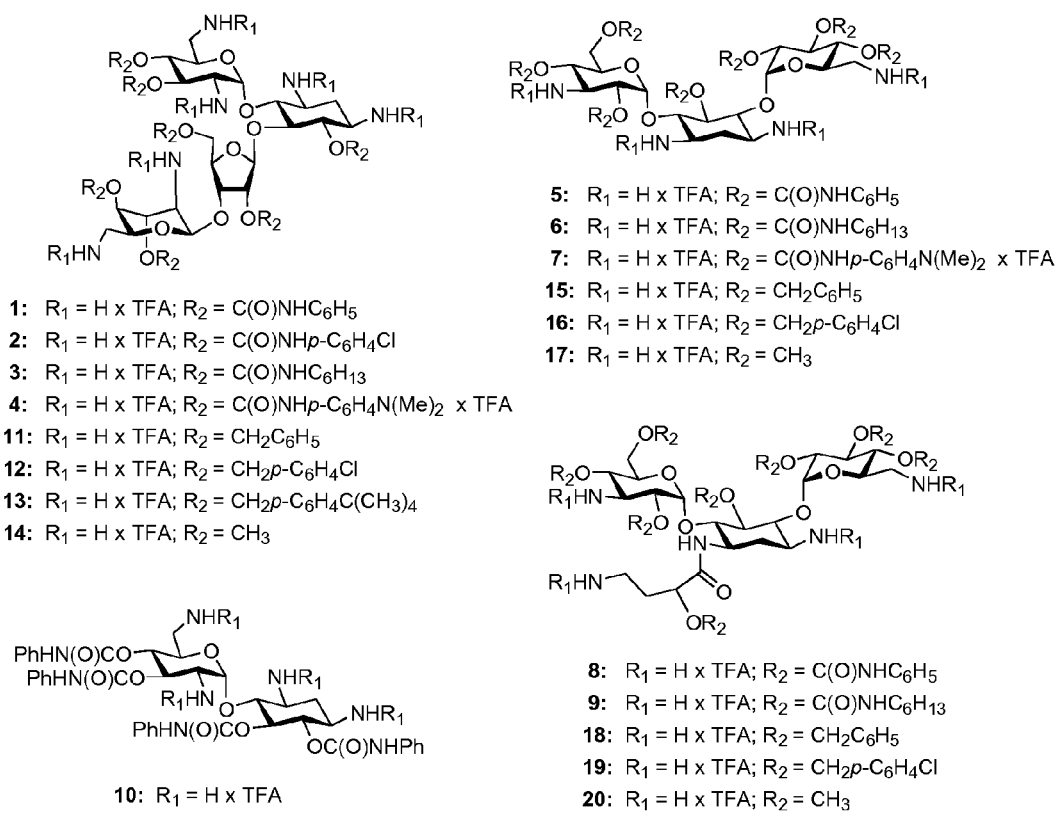
FIG. 1 Amphiphilic aminoglycoside antibiotics-derived polycarbamates 1-10 and polyethers 11-20.

The antibacterial activities of 20 aminoglycoside antibiotics-derived cationic amphiphiles were explored (FIG. 1). Four different oligocationic aminoglycoside-based polyol scaffolds (Neomycin B, Kanamycin A, Amikacin and Neamine) were selected in order to study how chemical modifications on aminoglycoside-based polyol scaffolds affect the antibacterial activity against Gram-positive, Gram-negative and multidrug-resistant strains of bacteria. The inventors focused on polyol modifications such as single-step conversion into hydrophobic polycarbamates and polyethers. It was hypothesized that conversion of polar aminoglycoside antibiotics into oligocationic amphiphiles provides a general tool to restore antibacterial activity in this old class of antibiotics.

C5"-modified Neomycin B-based polycationic lipids bearing $C_{16}$- or $C_{20}$-lipid chains have been shown to exhibit strong Gram-positive but reduced Gram-negative activity (Bera et al., 2008; Zhang et al., 2008; Zhang et al., 2009). The most potent Neomycin B-$C_{16}$-lipid conjugate in the form of the hexacationic TFA salt exhibited antibacterial activities against S. aureus (MIC=8 µg/mL), MRSE (MIC=2 µg/mL), E. coli ATCC 25922 (MIC=32 µg/mL) and P. aeruginosa (MIC=128 µg/mL) (Bera et al., 2008). However, exposure of this polycationic lipid to human red blood cells resulted in significant hemolytic activity (50% hemolysis at 200 µg/mL) (Zhang et al., 2009). The high hemolytic activity of this cationic lipid very likely does not permit systemic use and potential antibacterial applications are limited to use as disinfectants and antiseptics and as antibacterial agent in topical applications.

Interestingly, combinational studies using Neomycin B-$C_{16}$ lipid conjugate in combination with amikacin and vancomycin demonstrate synergistic effects against certain Gram-positive and Gram-negative strains, indicating a different mode of action (Zhang et al., 2009). Due to the structural similarity of the Neomycin B-$C_{16}$ lipid conjugate and the here described cationic polycarbamates and polyethers with other oligocationic amphiphiles, a membranolytic mode of action appears to be likely. Previous studies on (oligo)cationic surfactants, peptides, peptidomimetics, lipopeptides and lipids have shown that cationic amphiphiles target the lipid bilayer of bacteria resulting in enhanced permeability of the bacterial cell wall (Hancock and Sahl, 2006; Zasloff, 2002; Shai et al., 2006; Palermo and Kuroda, 2009; Gilbert and Moore, 2005). Although other mechanisms such as enzyme inactivation, denaturation of cell proteins and RNA-binding have been proposed (Park et al., 1998).

Evidence for a different antibacterial mode of action of polyol substituted aminoglycoside antibiotics-derived amphiphiles when compared to their parent aminoglycosides is provided by the inactivity of the cationic polymethyl ethers 14, 17 and 20. The necessity for a hydrophobic polyol substituent is consistent with the amphiphilic nature of other cationic antibacterials with proven membranolytic mode of actions such as cationic antibacterial peptides, lipopeptides and cationic lipids and surfactants. However, due to the polycationic nature of aminoglycoside antibiotics-derived amphiphiles, RNA-mediated interactions are likely especially after enhanced permeability of the bacterial cell membrane. Synergistic effects of aminoglycoside antibiotics with membrane permeabilizing agents are well documented (Shelburne et al., 2004; Drew et al., 2009).

Neomycin B-based hexacationic heptaphenylcarbamate 1 was found to exhibit potent antibacterial activity against multidrug-resistant Gram-positive MRSE (MIC=0.5 µg/mL) and MRSA (MIC=1 µg/mL). In contrast, the tetracationic Kanamycin A (5)-, Amikacin (8)- and Neamine (10)-based polyphenylcarbamates exhibit up to 64-fold reduced Gram-positive activity indicating that the nature of the polyol scaffold, the number of positive charges and number of hydrophobic groups influence the antibacterial Gram-positive activity. Compound 1 (MW=2132.6) also exhibits good Gram-negative activity against three strains of E. coli (MIC 16-32 µg/mL) especially when considering the high molecular weight. Although the MIC is 2-8 fold reduced when compared to Neomycin B sulfate (MW=908.9) susceptible E. coli, the activity is comparable to Neomycin B when the increase in molecular weight is taken into account. A rather surprising result is the observed potent activity of 1 against Neomycin B-resistant Gram-negative S. maltophilia (MIC=4 µg/mL) which is 32-64-fold lower when compared to amphiphilic di- and tetracationic lipopeptides (Serrano et al., 2009). In addition, good activity is also seen against A. baumannii (MIC=32 µg/mL). A. baumannii and S. maltophilia are opportunistic nosocomial pathogens found mostly in intensive care units (Gales et al., 2001). These microorganisms are known to be frequently resistant to many commonly used antimicrobial classes including the β-lactams and fluoroquinolones and as a result new chemotherapeutic options are in high demand (Ribera et al., 2002).

Replacement of the polyphenylcarbamate substituent by polybenzylethers also produces highly potent antibacterials. The most potent hexacationic Neomycin B-based heptabenzylether 11 displays slightly decreased Gram-positive activity (MIC 2-4 µg/ml) against S. aureus, MRSA, S. epidermidis and MRSE when compared to its Neomycin B-based polycarbamate analog 1. However, enhanced Gram-negative activity is observed against E. coli, P. aeruginosa and A. baumannii while a slight 2-fold decrease is observed against S. maltophilia. A rather unexpected result is the observed aromatic substitution effect on the antibacterial activity in both the cationic polycarbamates and polyethers. For instance, it was consistently observed that incorporation of a p-substituent into the aromatic ring of polyol-substituted phenylcarbamates and benzylethers in the Neomycin B, Kanamycin A and Amikacin scaffolds results in a 4-64-fold decrease in antibacterial activity. The observed substituent effect is rather unexpected and indicates that other factors besides the cationic charges and amphiphilicity contribute to the observed antibacterial activity in this class of compounds. Based on the potent antibacterial activity of Neomycin B-based amphiphiles 1 and 11 against Neomycin B-susceptible and resistant strains relative to other aminoglycoside-based and polyol-modified amphiphiles such as Kanamycin A, Amikacin and Neamine, it appears that the Neomycin B-based scaffold exhibits superior antibacterial properties.

In the present study, it has been established that polyol-substituted aminoglycoside antibiotics-derived cationic amphiphiles form a novel class of antibacterial agents with broad spectrum Gram-positive and Gram-negative activity. The amphiphilic nature of the oligocationic aminoglycoside antibiotics-derived amphiphile is crucial for their antibacterial activity while O-methylation of the polyol scaffold abolishes antibacterial activity. Neomycin B and Amikacin-based polyol-modified cationic amphiphiles display consistently higher antibacterial activities when compared to Kanamycin A, indicating that the nature of the aminoglycoside antibiotics-derived polyol influences the antibacterial potency. The most potent compounds 1, 9 and 11 exhibit significantly improved antibacterial activity against resistant strains when compared to their parent compounds Neomycin B and Amikacin while retaining their antibacterial activity against most Neomycin B- and Amikacin-susceptible bacterial strains. Unsubstituted phenyl rings in the form of polyphenylcarbamates or polyphenylether consistently exhibit higher antibacterial activities when compared to their para-substituted analogs. The observed aromatic substitution effects suggest that the antibacterial mode of action of polyol-substituted aminoglycoside antibiotics-derived amphiphiles involves other factors besides polycationic charges and amphiphilicity. Other potential mode of actions may involve selective binding to lipid A and other lipopolysaccharides (Vaara, 1996) as well as wall-associated teichoic acids, and RNA-mediated interactions (Davis, 1987; Arya, 2007).

I. Aminoglycoside Antibiotic Resistance

There are three general mechanisms of aminoglycoside antibiotic-resistance: (1) reduction of the intracellular concentration of the antibiotic within bacterial cells, usually via efflux of the agent out of the bacterial cell by either dedicated or general efflux pumps or other mechanisms; (2) alteration of the molecular target of the antibiotic, usually as result of a spontaneous mutation in the gene encoding the target or substitution of the target's function by an exogenous gene; and (3) enzymatic inactivation of the aminoglycoside (Neu, 1992; Hayes and Wolf, 1990; Jacoby et al., 1991). The rapid emergence of aminoglycoside antibiotic-resistant strains has instigated research efforts to develop novel aminoglycoside antibiotics or modified aminoglycoside antibiotic-analogs that can delay or avoid acquired resistance by pathogenic bacteria. However, progress has been slow due to the fact that novel and purely synthetic aminoglycoside antibiotics are difficult to synthesize and structural modifications on naturally occurring aminoglycoside antibiotics usually require complex multi-step organic synthesis.

Most of the naturally occurring aminoglycoside antibiotics are structurally characterized by amino sugars glycosidically linked to an aminocyclitol which, in most cases, is 2-deoxystreptamine. Several types of 2-deoxy-streptamine derivatives exist: monosubstituted derivatives such as neamine, 4,5-disubstituted (neomycin type derivatives), and 4,6-disubstituted (kanamycin, tobramycin and gentamycin) derivatives. aminoglycoside antibiotics carry up to six amino groups which are predominantly charged at physiological pH (Dorman et al., 1976; Botto and Coxon, 1983) and bind with high affinity to anions and nucleic acids via electrostatic and hydrogen bonding interactions (Ohyama et al., 1998; Chen et al., 1997; Wang and Tor, 1997; Constantinou-Kokotou et al., 2001). Aminoglycoside antibiotics are considered to be non-specific RNA binders that recognize numerous three-dimensional RNA structures including group I introns (Von Ahsen and Noller, 1993), hammerhead ribozymes (Clouet-d'Orval et al., 1995), the HIV-1's TAR (Mei et al., 1995) and RRE (Werstuck et al., 1996; Kirk et al., 2000) regulatory domains. In order to exhibit their antibacterial activity, aminoglycoside antibiotics must bind to the RNA receptor located within the cell. This requires uptake of the aminoglycoside antibiotic by the bacterial cell. However, aminoglycoside antibiotic-resistance may be manifested by reduced drug uptake as a result of activation of drug efflux pumps, modified membrane potential, changes in membrane composition and other factors (Taber et al., 1987).

II. Pharmaceutical Formulations and Administration

Pharmaceutical compositions of the present invention comprise an effective amount of one or more candidate substances (e.g., an aminoglycoside derivative or any other hydrophobically enhanced aminoglycoside) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient, such as a pharmaceutically acceptable carrier, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. Compounds of the present invention may be administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, via localized perfusion, bathing target cells directly, or by other method or any combination of the foregoing as would be known to one of ordinary skill in the art (see, for example, Remington's Pharmaceutical Sciences, 1990). In particular embodiments, the composition may be formulated for oral delivery. In certain embodiments, intramuscular, intravenous, topical administration, or inhalation administration is contemplated. Pharmaceutical compositions comprising a compound of the present invention are also contemplated, and such compositions may be adapted for administration via any method known to those of skill in the art, such as the methods described above.

In particular embodiments, the composition is administered to a subject using a drug delivery device. Any drug delivery device is contemplated for use in delivering a pharmaceutically effective amount of an aminoglycoside derivative or any other hydrophobically enhanced aminoglycoside described herein.

The actual dosage amount of an aminoglycoside derivative or any other hydrophobically enhanced aminoglycoside described herein administered to an animal patient can be determined by physical and physiological factors such as body weight, severity of condition, the type of disease being treated, previous or concurrent therapeutic interventions, idiopathy of the patient and on the route of administration. The practitioner responsible for administration will typically determine the concentration of active ingredient(s) in a composition and appropriate dose(s) for the individual subject. Compounds of the present invention may, in certain embodiments, be cleared by the kidneys: thus, it may, in certain embodiments, be important to assess any underlying problems with kidney function. Kidney function may be assessed by measuring the blood levels of creatinine, a protein normally found in the body. If these levels are higher than normal, it is an indication that the kidneys may not be functioning at an optimal rate and dosage may be lowered accordingly The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent, for example. The administration could be intra-operative or post-operative.

In certain embodiments, pharmaceutical compositions may comprise, for example, at least about 0.1% of an aminoglycoside derivative or any other hydrophobically enhanced aminoglycoside described herein. In other embodiments, an aminoglycoside derivative or any other hydrophobically enhanced aminoglycoside described herein may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The aminoglycoside derivative or any other hydrophobically enhanced aminoglycoside described herein may be formulated into a composition, such as a pharmaceutical composition, in a free base, neutral, or salt form. Pharmaceutically acceptable salts are described herein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents (e.g., glucose, lactose, or mannitol), assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Sterile injectable solutions may be prepared by incorporating a compound of the present invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

III. Combination Therapy

In order to enhance or increase the effectiveness of an aminoglycoside derivative or any other hydrophobically enhanced aminoglycoside described herein, the conjugate may be combined with another therapy, such as another agent that combats and/or prevents bacterial infection. For example, aminoglycoside derivatives of the present invention may be provided in a combined amount with an effective amount of an anti-bacterial agent (that is, an antibiotic). Anti-bacterial classes and agents are well-known in the art, and include, for example, the classes of aminoglycoside antibiotics, cephalosporins, penicillins, quinolones, sulfonamides, tetracyclines, beta-lactams and macrolides. Non-limiting specific examples of antibacterial agents include linezolid, tigecycline, tetracycline, oxytetracycline, doxycycline, minocycline, vancomycin, enrofloxacin, erythromycin, tyrocidine, griseofulvin, streptomycin, polymyxin, cephalosporin, ampicillin, cephalothin, lincomycin, gentamicin, carbenicillin, cephalexin and clindamycin. These lists of antibiotics are not exhaustive and one skilled in the art can readily determine other antibiotics which may be employed.

An aminoglycoside derivative or any other hydrophobically enhanced aminoglycoside described herein may be combined with, for example, a lipid bilayer permeabilizing agent, such as an ionic lipid or other such agent known in the art. See, e.g., Shelburne et al., 2004.

It is contemplated that combination therapy of the present invention may be used in vitro or in vivo. These processes may involve administering the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein an aminoglycoside derivative or any other hydrophobically enhanced aminoglycoside described herein is "A" and a second agent, such as an anti-bacterial agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

IV. Chemical Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —SiH$_3$ (see below for definitions of group(s) containing the term silyl, e.g., alkylsilyl).

The symbol "—" means a single bond, "=" means a double bond, and "≡" means triple bond. The symbol " ---- " represents a single bond or a double bond. The symbol " ⋀⋀ ", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄▬" means a single bond where the group attached to the thick end of the wedge is "out of the page." The symbol "⫴⫴⫴" means a single bond where the group attached to the thick end of the wedge is "into the page". The symbol " ⋀⋀ " means a single bond where the conformation is unknown (e.g., either R or S), the geometry is unknown (e.g., either E or Z) or the compound is present as mixture of conformation or geometries (e.g., a 50%/50% mixture).

When a group "R" is depicted as a "floating group" on a ring system, for example, in the formula:

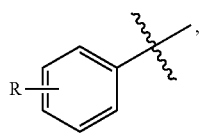

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

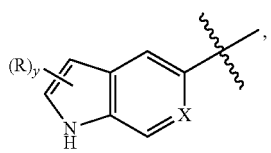

then R may replace any hydrogen attached to any of the ring atoms of either of the fuzed rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

When y is 2 and "(R)$_y$" is depicted as a floating group on a ring system having one or more ring atoms having two replaceable hydrogens, e.g., a saturated ring carbon, as for example in the formula:

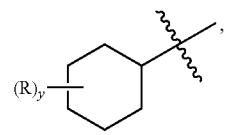

then each of the two R groups can reside on the same or a different ring atom. For example, when R is methyl and both R groups are attached to the same ring atom, a geminal dimethyl group results. Where specifically provided for, two R groups may be taken together to form a divalent group, such as one of the divalent groups further defined below. When such a divalent group is attached to the same ring atom, a spirocyclic ring structure will result.

When the point of attachment is depicted as "floating", for example, in the formula:

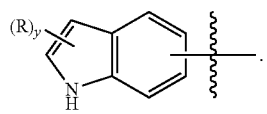

then the point of attachment may replace any replaceable hydrogen atom on any of the ring atoms of either of the fuzed rings unless specified otherwise.

In the case of a double-bonded R group (e.g., oxo, imino, thio, alkylidene, etc.), any pair of implicit or explicit hydrogen atoms attached to one ring atom can be replaced by the R group. This concept is exemplified below:

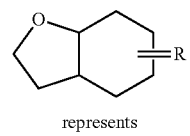

represents

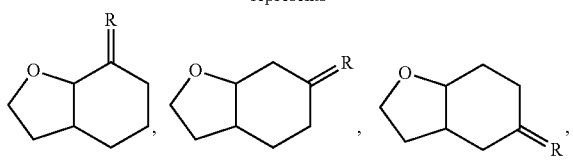

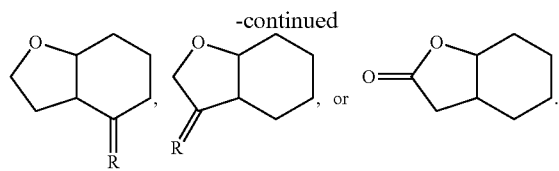

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question, e.g., it is understood that the minimum number of carbon atoms in the group "alkenyl$_{(C≤18)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two CT-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

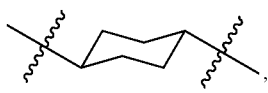 [SMILES: *C1CCC(*)CC1]

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and CH=CHBr, are non-limiting examples of substituted alkenyl groups.

The term "alkenediyl" when used without the "substituted" modifier refers to a non-aromatic divalent group, wherein the alkenediyl group is attached with two 6-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH, —CH=C(CH$_3$)CH$_2$, CH=CHCH$_2$—, and

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkynediyl" when used without the "substituted" modifier refers to a non-aromatic divalent group, wherein the alkynediyl group is attached with two CT-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH═CH$_2$ (vinylphenyl), —C$_6$H$_4$CH═CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$—OCH$_3$, —C$_6$H$_4$—OCH$_2$CH$_3$, —C$_6$H$_4$OC(O)CH$_3$, —C$_6$H$_4$—NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$—NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

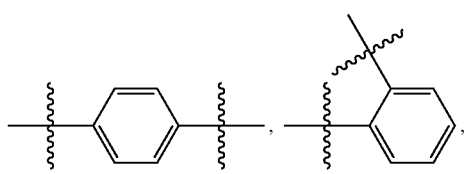

-continued

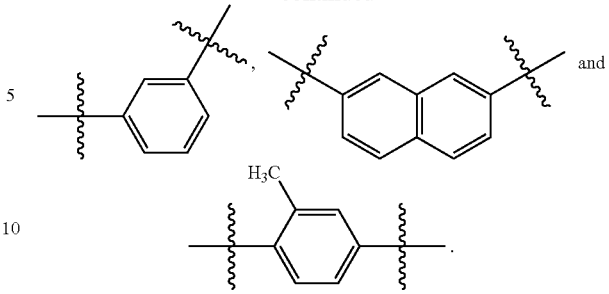

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are carbon, and wherein the divalent group further has at least one atom independently selected from the group consisting of N, O, F, Cl, Br, I, Si, P, and S.

The term "aralkyl" when used without the "substituted" modifier refers to the monovalent group -alkane-diylaryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, —Cl, Br, I, Si, and P.

The term "heteroarenediyl" when used without the "substituted" modifier refers to a divalent group, wherein the heteroarenediyl group is attached with two CT-bonds, with an aromatic carbon atom or nitrogen atom as the point of attachment, said carbon atom or nitrogen atom forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. Non-limiting examples of heteroarenediyl groups include:

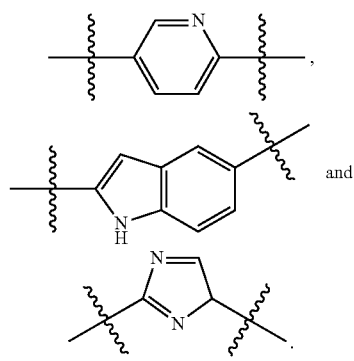

and

The term "substituted heteroarenediyl" refers to a divalent group, wherein the heteroarenediyl group is attached with two σ-bonds, with an aromatic carbon atom or nitrogen atom as points of attachment, said carbon atom or nitrogen atom forming part of one or more six-membered aromatic ring structure(s), wherein at least one of the ring atoms is nitrogen, oxygen or sulfur, and wherein the divalent group further has at least one atom independently selected from the group consisting of non-aromatic nitrogen, non-aromatic oxygen, non aromatic sulfur F, —Cl, Br, I, Si, and P.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, —N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, hetero aryl amino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as NHR, in which R is substituted acyl, as that term is defined above. The groups —NHC(O)OCH$_3$ and —NHC(O)NHCH$_3$ are non-limiting examples of substituted amido groups.

The term "alkylimino" when used without the "substituted" modifier refers to the group =NR, wherein the alkylimino group is attached with one σ-bond and one π-bond, in which R is an alkyl, as that term is defined above. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "fluoroalkyl" when used without the "substituted" modifier refers to an alkyl, as that term is defined above, in which one or more fluorines have been substituted for hydrogens. The groups, —CH$_2$F, —CF$_2$H, —CF$_3$, and —CH$_2$CF$_3$ are non-limiting examples of fluoroalkyl groups. The term "substituted fluoroalkyl" refers to a non-aromatic monovalent group with a saturated carbon atom as the point of attachment, a linear or branched, cyclo, cyclic or acyclic structure, at least one fluorine atom, no carbon-carbon double or triple bonds, and at least one atom independently selected from the group consisting of N, O, Cl, Br, I, Si, P, and S. The following group is a non-limiting example of a substituted fluoroalkyl: —CFHOH.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "substituted alkylphosphate" refers to the group —OP(O)(OH)(OR), in which R is a substituted alkyl, as that term is defined above.

The term "dialkylphosphate" when used without the "substituted" modifier refers to the group —OP(O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include: —OP(O)(OMe)$_2$, —OP(O)(OEt)(OMe) and —OP(O)(OEt)$_2$. The term "substituted dialkylphosphate" refers to the group —OP(O)(OR)(OR'), in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached via the oxygen atoms to the phosphorous.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)$_2$R, in which R is an alkyl, as that term is defined above. Non-limiting examples of alkylsulfonyl groups include: —S(O)$_2$CH$_3$, —S(O)$_2$CH$_2$CH$_3$, —S(O)$_2$CH$_2$CH$_2$CH$_3$, S(O)$_2$CH(CH$_3$)$_2$, —S(O)$_2$CH(CH$_2$)$_2$, —S(O)$_2$-cyclopentyl, and —S(O)$_2$-cyclohexyl. The term "substituted alkylsulfonyl" refers to the group —S(O)$_2$R, in which R is a substituted alkyl, as that term is defined above. For example, —S(O)$_2$CH$_2$CF$_3$ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted" modifier, refers to groups, defined as —S(O)$_2$R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)$_2$R, in which R is substituted alkenyl, alkynyl, aryl, aralkyl, heteroaryl and heteroaralkyl, respectively.

The term "alkylsulfinyl" when used without the "substituted" modifier refers to the group —S(O)R, in which R is an alkyl, as that term is defined above. Non-limiting examples of alkylsulfinyl groups include: —S(O)CH$_3$, —S(O)CH$_2$CH$_3$, —S(O)CH$_2$CH$_2$CH$_3$, —S(O)CH(CH$_3$)$_2$, —S(O)CH(CH$_2$)$_2$, —S(O)-cyclopentyl, and —S(O)-cyclohexyl. The term "substituted alkylsulfinyl" refers to the group —S(O)R, in which R is a substituted alkyl, as that term is defined above. For example, —S(O)CH$_2$CF$_3$ is a substituted alkylsulfinyl group.

Similarly, the terms "alkenylsulfinyl", "alkynylsulfinyl", "arylsulfinyl", "aralkylsulfinyl", "heteroarylsulfinyl", and "heteroaralkylsulfinyl" when used without the "substituted" modifier, refers to groups, defined as —S(O)R, in which R is alkenyl, alkynyl, aryl, aralkyl, heteroaryl, and heteroaralkyl, respectively, as those terms are defined above. When any of the terms alkenylsulfinyl, alkynylsulfinyl, arylsulfinyl, aralkylsulfinyl, heteroarylsulfinyl, and heteroaralkylsulfinyl is modified by "substituted," it refers to the group —S(O)R, in which R is substituted alkenyl, alkynyl, aryl, aralkyl, heteroaryl and heteroaralkyl, respectively.

The term "alkylammonium" when used without the "substituted" modifier refers to a group, defined as —NH$_2$R$^+$, —NHRR'$^+$, or —NRR'R"$^+$, in which R, R' and R" are the same or different alkyl groups, or any combination of two of R, R' and R" can be taken together to represent an alkanediyl. Non-limiting examples of alkylammonium cation groups include: —NH$_2$(CH$_3$)$^+$, —NH$_2$(CH$_2$CH$_3$)$^+$, —NH$_2$(CH$_2$CH$_2$CH$_3$)$^+$, —NH(CH$_3$)$_2$$^+$, —NH(CH$_2$CH$_3$)$_2$$^+$, —NH(CH$_2$CH$_2$CH$_3$)$_2$$^+$, —N(CH$_3$)$_3$$^+$, —N(CH$_3$)(CH$_2$CH$_3$)$_2$$^+$, —N(CH$_3$)$_2$(CH$_2$CH$_3$)$^+$, —NH$_2$C(CH$_3$)$_3$$^+$, —NH(cyclopentyl)$_2$$^+$, and —NH$_2$(cyclohexyl)$^+$. The term "substituted alkylammonium" refers —NH$_2$R$^+$, —NHRR'$^+$, or —NRR'R"$^+$, in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more carbon atoms, at least two of which are attached to the nitrogen atom shown in the formula.

The term "alkylsulfonium" when used without the "substituted" modifier refers to the group —SRR'$^+$, in which R and R' can be the same or different alkyl groups, or R and R' can be taken together to represent an alkanediyl. Non-limiting examples of alkylsulfonium groups include: SH(CH$_3$)$^+$, SH(CH$_2$CH$_3$)$^+$, SH(CH$_2$CH$_2$CH$_3$)$^+$, —S(CH$_3$)$_2$, —S(CH$_2$CH$_3$)$_2$, —S(CH$_2$CH$_2$CH$_3$)$_2$, —SH(cyclopentyl)$^+$, and —SH(cyclohexyl)$^+$. The term "substituted alkylsulfonium" refers to the group SRR'$^+$, in which R and R' can be the same or different substituted alkyl groups, one of R or R' is an alkyl and the other is a substituted alkyl, or R and R' can be taken together to represent a substituted alkanediyl. For example, —SH(CH$_2$CF$_3$)$^+$ is a substituted alkylsulfonium group.

The term "alkylsilyl" when used without the "substituted" modifier refers to a monovalent group, defined as —SiH$_2$R, —SiHRR', or —SiRR'R", in which R, R' and R" can be the same or different alkyl groups, or any combination of two of R, R' and R" can be taken together to represent an alkanediyl. The groups, —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups. The term "substituted alkylsilyl" refers to —SiH$_2$R, —SiHRR', or —SiRR'R", in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

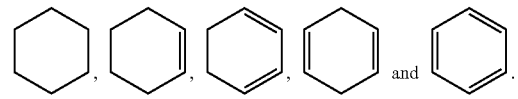

As will be understood by a person of skill in the art, no one such ring atom forms part of more than one double bond.

Any undefined valency on an atom of a structure shown in this application implicitly represents a hydrogen atom bonded to the atom.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002), As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, $-[-CH_2CH_2-]_n-$, the repeat unit is $-CH_2CH_2-$. The subscript "n" denotes the degree of polymerisation, that is, the number of repeat units linked together. When the value for "n" is left undefined, it simply designates repetition of the formula within the brackets as well as the polymeric nature of the material. The concept of a repeat unit applies equally to where the connectivity between the repeat units extends three dimensionally, such as in metal organic frameworks, cross-linked polymers, thermosetting polymers, etc.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), —Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five, and optionally amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Tip, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and haloethoxycarbonyl groups (such as β,β,β-trichloroethoxycarbonyl and β-iodoethoxycarbonyl).

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. Examples

The following examples are included to demonstrate particular embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Synthesis of Amphiphilic Cationic Polycarbamates and Polyethers

Figure 2:
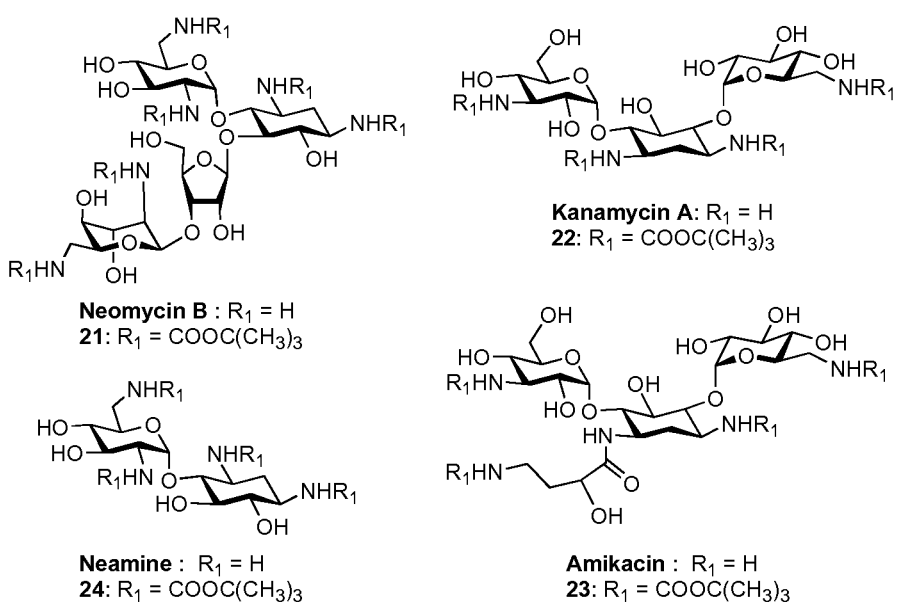
FIG. 2 Structures of unprotected and Boc-protected aminoglycoside antibiotics used for conversion into amphiphilic polycarbamtes and polyethers.

Neomycin B and Kanamycin A (FIG. 2) were selected due to their commercial availability in multi gram quantities and low price. Moreover, the low antibacterial activity of Neomycin B and Kanmaycin A towards several multi-drug resistant bacteria including methicillin-resistant *Staphylococcus aureus* (MRSA), *Pseudomonas aeruginosa* and *Stenotrophomonas maltophilia* was an additional incentive to develop novel analogs with reduced resistance and increased activity. Amikacin was selected due to its potent Gram-positive and Gram-negative activity while Neamine was chosen as a minimal Neomycin B mimetic to explore size effects (FIG. 2). The amphiphilic Neomycin B-derived polycarbamates 1-4, the Kanamycin A-derived polycarbamates 5-7, the Amikacin-derived polycarbamates 8 and 9 the Neamine-derived polycarbamate 10 were prepared from the corresponding amino protected tertbutyl carbamates (Boc) of the corresponding aminoglycosides 21-24 (Quader et al., 2007; Disney, M. D.; Barrett, 2007; Albert et al., 1985; Kim et al., 2004) (FIG. 1)

via carbamoylation of the hydroxy groups with various commercially available hydrophobic isocyanates including phenylisocyanate, 4-chloro-phenylisocyanate, hexylisocyanate and 4-N,N,-dimethyl-phenylisocyante in pyridine (Scheme 1) (Agrawal and Khorana, 1972).

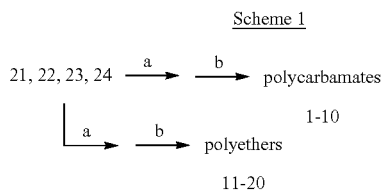

Scheme 1

$^{a}$Reagents and conditions: R$_2$NCO, pyridine, DMF; $^{b}$TFA, 0° C., 3 min; $^{c}$Ba(OH)$_2$, DMF, benzyl bromide or MeI Deblocking of the Boc group using trifluoroacetic acid afforded the cationic and amphiphilic polycarbamates 1-10 in the form of their TFA salts. Analogously, the cationic and amphiphilic polyethers 11-20 were prepared form the corresponding Boc-protected aminoglycosides 21-23 via O-alkylation with reactive alkyl bromides such as benzylbromide, 4-chlorobenzylbromide, 4-tertbutyl benzylbromide and methyl iodide using bariumhydroxide in DMF (Kuhn et al., 1958) (Scheme 1) followed by deblocking of the amino protecting groups to produce Neomycin B-derived polyethers 11-14, Kanamycin A-derived polyethers 15-17 and Amikacin-derived polyethers 18-20 (FIG. 1).

Example 2

Antibacterial Testing of Amphiphilic Cationic Polycarbamates and Polyethers

All compounds were tested against American Type Culture Collection (ATCC) reference strains as well as clinical isolates from the Canadian Intensive Care Unit (CAN-ICU) study (Zhanel, et al., 2008). Isolates tested included: *S. aureus* ATCC 29213, methicillin-resistant *Staphylococcus aureus* (MRSA) ATCC 33592, *S. epidermidis* ATCC 14990, methicillin-resistant *Staphylococcus epidermidis* (MRSE) (Cefazolin-CZ MIC>32 m/mL) CAN-ICU 61589, *Enterococcus faecalis* ATCC 29212, *E. faecium* ATCC 27270, *Streptococcus pneumoniae* ATCC 49619, *E. coli* ATCC 25922, *E. coli* (Gentamicin-resistant MIC>32 m/mL) CAN-ICU 61714, *E. coli* (Amikacin MIC 32 m/mL) CAN-ICU 63074, *Pseudomonas aeruginosa* ATCC 27853 and *P. aeruginosa* (Gent-R MIC>32 m/mL) CAN-ICU 62308, *Stenotrophomonas maltophilia* (CAN-ICU 62585), *Acinetobacter* baumanni (CAN-ICU 63169) and *S. pneumoniae* ATCC 13883. Antibacterial activity against Gram-positive and Gram-negative microorganisms was performed via broth macrodilution tests using CLSI methodology (Clinical and Laboratory Standards Institute, 2006). The minimum inhibitory concentration (MIC) in μg/mL of the aminoglycoside-derived amphiphilic polycarbamates and polyethers were determined using established methods (Clinical and Laboratory Standards Institute, 2006) and are shown in Tables 1 and 2, respectively.

TABLE 1

Minimal Inhibitory Concentrations (MIC) in μg/mL for Various Bacterial Strains Against Neomycin B-, Kanamycin A-, Amikacin-, and Neamine-derived Oligocationic Polycarbamates 1-11.

| Control Organism | Gentamicin | Neomycin B | 1 | 2 | 3 | 4 | Kanamycin A | 5 | 6 | 7 | Amikacin | 8 | 9 | 10 |
|---|---|---|---|---|---|---|---|---|---|---|---|---|---|---|
| *S. aureus*$^a$ | 1 | 1 | 1 | 64 | 2 | 16 | 4 | 32 | 32 | 16 | 4 | 8 | 4 | 16 |
| MRSA$^b$ | 2 | 256 | 1 | 64 | 256 | 16 | >512 | 32 | 64 | 32 | 8 | 16 | 4 | 16 |
| *S. epidermidis*$^c$ | 0.25 | 0.25 | 0.5 | 16 | 1 | 8 | 2 | 4 | 16 | 16 | 1 | 2 | 4 | 8 |
| MRSE$^d$ | 32 | 0.5 | 0.5 | 32 | 2 | 8 | 128 | 8 | 32 | 32 | 2 | 2 | 4 | 8 |
| *S. pneumoniae*$^e$ | 4 | 32 | 16 | 128 | 8 | 32 | 8 | 64 | 128 | >256 | 8 | 32 | 32 | >256 |
| *E. coli*$^f$ | 1 | 4 | 32 | >256 | 8 | 128 | 8 | >256 | 128 | 256 | 4 | 256 | 4 | 32 |
| *E. coli*$^g$ | 128 | 8 | 16 | >256 | 8 | 128 | 16 | >256 | 64 | 256 | 2 | 256 | 8 | 32 |
| *E. coli*$^h$ | 8 | n.d. | 16 | 256 | 32 | 64 | 32 | >256 | 64 | 256 | 32 | 256 | 4 | 32 |
| *P. aeruginosa*$^i$ | 8 | 512 | 256 | >256 | >256 | 128 | >512 | >256 | 128 | >256 | 4 | >256 | 64 | 128 |
| *P. aeruginosa*$^j$ | 128 | 512 | 128 | 256 | 256 | 128 | >512 | >256 | 32 | 256 | 128 | 256 | 16 | 128 |
| *S. maltophilia*$^k$ | >512 | >512 | 4 | 128 | >256 | 256 | >512 | >256 | >256 | >256 | >512 | 128 | 16 | 64 |
| *A. baumannii*$^l$ | 128 | 64 | 32 | >256 | >256 | >256 | 32 | >256 | >256 | >256 | 128 | 256 | >128 | 256 |
| *S. pneumoniae*$^m$ | 0.25 | 1 | 256 | 256 | 4 | >256 | 1 | >256 | >256 | >256 | 0.5 | 256 | >128 | 64 |

$^a$ATCC 29213.
$^b$Methicillin-resistant *S. aureus* ATCC 33592.
$^c$ATCC 1490.
$^d$Methicillin-resistant *S. epidermidis* (ATCC 14990).
$^e$ATCC 49619.
$^f$ATCC 25922.
$^g$ATCC 6174 (gentamicin resistant).
$^h$CAN-ICU 63074.
$^i$ATCC 27853.
$^j$CAN-ICU 62308.
$^k$CAN-ICU 62584.
$^l$CAN-ICU 63169.
$^m$ATCC 13883.
n.d. = not determined.

TABLE 2

Minimal Inhibitory Concentrations (MIC) in µg/mL for Various Bacterial Strains
Against Neomycin B-, Kanamycin A- and Amikacin-derived Oligocationic Polyethers 12-21.

| Control Organism | Gentamicin | Neomycin B | 11 | 12 | 13 | 14 | Kanamycin A | 15 | 16 | 17 | Amikacin | 18 | 19 | 20 |
|---|---|---|---|---|---|---|---|---|---|---|---|---|---|---|
| S. aureus[a] | 1 | 1 | 4 | 64 | 128 | >256 | 4 | 8 | 32 | >256 | 4 | 4 | 128 | >256 |
| MRSA[b] | 2 | 256 | 4 | 64 | 128 | >256 | >512 | 8 | 32 | >256 | 8 | 4 | 128 | >256 |
| S. epidermidis[c] | 0.25 | 0.25 | 2 | 32 | 64 | 256 | 2 | 4 | 32 | 256 | 1 | 1 | 128 | >256 |
| MRSE[d] | 32 | 0.5 | 2 | 64 | 64 | >256 | 128 | 8 | 16 | >256 | 2 | 1 | 64 | >256 |
| S. pneumoniae[e] | 4 | 32 | 16 | 128 | 256 | >256 | 8 | 32 | 64 | >256 | 8 | 32 | 128 | >256 |
| E. coli[f] | 1 | 4 | 8 | 128 | 128 | >256 | 8 | 32 | 128 | >256 | 4 | 16 | >256 | >256 |
| E. coli[g] | 128 | 8 | 16 | >128 | 128 | >256 | 16 | 32 | 128 | >256 | 2 | 16 | >256 | >256 |
| E. coli[h] | 8 | n.d. | 4 | 64 | 128 | >256 | 32 | 16 | 64 | >256 | 32 | 16 | 256 | >256 |
| P. aeruginosa[i] | 8 | 512 | 32 | >128 | 256 | >256 | >512 | >64 | >128 | >256 | 4 | 128 | >256 | >256 |
| P. aeruginosa[j] | 128 | 512 | 64 | >128 | 128 | >256 | >512 | >64 | >128 | >256 | 128 | 64 | >256 | >256 |
| S. maltophilia[k] | >512 | >512 | 8 | >128 | >128 | >256 | >512 | >64 | >128 | >256 | >512 | 32 | >256 | >256 |
| A. baumannii[l] | 128 | 64 | 16 | >128 | >128 | >256 | 32 | >64 | >128 | >256 | 128 | 32 | >256 | >256 |
| S. pneumoniae[m] | 0.25 | 1 | 8 | 128 | >128 | >256 | 1 | >64 | >128 | >256 | 0.5 | 16 | >256 | >256 |

[a]ATCC 29213.
[b]Methicillin-resistant S. aureus ATCC 33592.
[c]ATCC 1490.
[d]Methicillin-resistant S. epidermidis (ATCC 14990).
[e]ATCC 49619.
[f]ATCC 25922.
[g]ATCC 6174 (gentamicin resistant).
[h]CAN-ICU 63074.
[i]ATCC 27853.
[j]CAN-ICU 62308.
[k]CAN-ICU 62584.
[l]CAN-ICU 63169.
[m]ATCC 13883.

The results show that the nature of the cationic scaffold (Neomycin B, Kanamycin A, Amikacin and Neamine) and the nature of the polyol substituent (hydrophobic carbamate or ether) influence the antibacterial activity and strain specific susceptibility. The most potent Neomycin B-derived heptaphenylcarbamate 1 exhibits excellent Gram-positive activity against S. aureus, MRSA, S. epidermidis and MRSE (MIC≤1 µg/mL). A remarkable 256-fold enhancement of 1 when compared to unmodified Neomycin B against MRSA is observed while at the same time the potent activity against Neomycin B-susceptible strains such as S. aureus, S. epidermidis, MRSE and S. pneumoniae is maintained and the molecular weight of 1 is more than doubled. Introduction of p-chloro, and p-dimethylamino substituents into the phenyl-ring of the polycarbamates results in significant loss of Gram-positive activity as observed for compounds 2-4. Slightly reduced activities are observed for 1 against Gram-negative E. coli while very little improvements are seen against P. aeruginosa. A very intriguing result is the potent activity of 1 against multidrug-resistant S. maltophilia (MIC=4 µg/mL) demonstrating an over 128-fold increased susceptibility over Neomycin B and a slightly increased activity against A. baumannii (MIC=32 µg/mL).

Replacement of the Neomycin B-based hexacationic scaffold by a tetracationic Kanamycin A-based scaffold results in reduced antibacterial activity. Kanamycin A-based amphiphilic heptacarbamates 5-7 exhibit significantly reduced Gram-positive activity (up to 32-fold) and little Gram-negative activity (MIC≥64 µg/mL) for most strains (except MRSA for compound 8) when compared to Neomycin B-based carbamates 1-4. Moreover, modifications on the Kanamycin A-based tetracationic scaffold influences the antibacterial activity. For instance, Amikacin-based tetracationic octaphenylcarbamate 8 and octahexylcarbamate 9 exhibit significantly improved Gram-positive activity (2-16-fold) when compared to their respective Kanamycin A-based heptacarbamates 5 and 6. Amikacin-derived tetracationic octacarbamates 8 and 9 are structurally related to Kanamycin A-derived tetracationic heptacarbamates 5 and 6 via amidation of N-3 of Kanamycin A with a L-hydroxyaminobuteroyl substituent. In addition, tetracationic octahexylcarbamate 9 shows 8-32-fold improvements against the Gram-negatives E. coli and S. maltophilia when compared to 6 indicating that subtle modifications on the Kanamycin A-based tetracationic scaffold can lead to significant improvements in the antibacterial activity. Moreover, reduction in the size of the aminoglycoside antibiotic does not abolish antibacterial activity. For instance, the Neamine-based tetracationic tetraphenylcarbamate 10 displays improved antibacterial activity against most Gram-positive strains and all Gram-negative strains when compared to Kanamycin A-based tetracationic hexaphenylcarbamate analog 5. However, 10 shows significantly reduced Gram-positive activity when compared to related hexacationic heptaphenylcarbamate 1 (16-fold reduction in MIC). This indicates that the neamine portion of neomycin as well as the lower portion of neomycin are required for optimal antibacterial activity. However, the relative potent antibacterial activity of 10 may indicate that the upper portion of neomycin may be more important for antibacterial activity.

A similar trend in the antibacterial activities is observed for the Neomycin B-, Kanamycin A- and Amikacin-based oligocationic polyethers 11-20 (Table 2). A variety of substituents including methyl, benzyl, p-chlorobenzyl, and p-tertbutyl ethers were evaluated. The most potent cationic polyether analogs in the order of activity are the Neomycin B-based hexacationic heptabenzyl ether 11, the Amikacin-based tetracationic octabenzylether 18 and Kanamycin A-based tetracationic heptaphenylether 15. The introduction of a chloro or tertbutyl substituent into the para-position of the phenyl ring greatly diminishes (16-32 fold increase in MIC) antibacterial activity. The most potent cationic polyether analog 11 exhibits broad-spectrum activity against Gram-positive and most Gram-negative strains tested. Of particular interest are the potent activities of 11 against the emerging multi drug resistant superbugs such as MRSE (MIC=2 µg/mL), MRSA (MIC=4 µg/mL) *S. maltophilia* (MIC=8 µg/mL), *A. baumannii* (MIC=16 µg/mL) and *P. aeruginosa* (two strains; MIC=32-64 µg/mL) strains while retaining good activity against non-resistant strains such as *S. epidermidis* (MIC=2 µg/mL), *S. aureus* (MIC=4 µg/mL), *E. coli* ATCC25922 (MIC=8 µg/mL) and *S. pneumoniae* (MIC=16 µg/mL). Moreover, the requirement for a hydrophobic ether substituent on the oligocationic aminoglycoside scaffold is apparent due to the fact that cationic polymethyl ethers 14, 17 and 20 do not exhibit antibacterial activities below an MIC of 256 µg/mL.

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference.

Agrawal et al., *J. Am. Chem. Soc.*, 94:3578-3585, 1972.
Albert et al., *J. Antibiot.*, 38:275-278, 1985.
Andrä et al., *Biochem. J.*, 385:135-143, 2005.
Arya, In: *Aminoglycoside antibiotics: From Chemical Biology to Drug Discovery*, John Wiley & Sons, 1-319, 2007.
Bera et al., *J. Med. Chem.*, 51:6160-6164, 2008.
Botto and Coxon, *J. Am. Chem. Soc.*, 105:1021-1028, 1983.
Boucher et al., *Clin. Infect. Dis.*, 48:1-12, 2009.
Chen et al., *Biochemistry*, 36:11402-11407, 1997.
Chen et al., *Infect. Dis. Clin. N. Am.*, 23:1053-1075, 2009.
Chongsiriwatana et al., *Proc. Natl. Acad. Sci. USA*, 105:2794-2799, 2008.
Chopra et al., *Antimicrob. Agents Chemother.*, 41:497-503, 1997.
Clinical and Laboratory Standards Institute, M100-S16. CLSI/NCCLS M100-S15, 2006.
Clouet-d'Orval et al., *Biochemistry*, 32:11186-11190, 1995.
Constantinou-Kokotou et al., *Bioorg. Med. Chem. Lett.*, 11:1015-1018, 2001.
David, *J. Mol. Recog.*, 14:370-387, 2001.
Davis, *Microbiol. Rev.*, 51:341-350, 1987.
Disney and Barrett, *Biochemistry*, 46:11223-11230, 2007.
Dorman et al., *J. Am. Chem. Soc.* 98:6885-6888, 1976.
Drew et al., *J. Am. Chem. Soc.*, 131:486-493, 2009.
Gales et al., *Clin. Infect. Dis.*, 32:S104-S113, 2001.
Gilbert and Moore, *J. Appl. Microbiol.*, 99:703-715, 2005.
Giuliano et al., *Kidney Int.*, 26:838-847, 1984.
Greene and Wuts, In: *Protective Groups in Organic Synthesis*, 2$^{nd}$ Ed.; Wiley, N.Y., 1999.
Hamuro et al., *J. Am. Chem. Soc.*, 121:12200-12201, 1999.
Hancock and Bell, *Eur. J. Clin. Microbiol. Infect. Dis.* 1988, 7, 713-720, 1988.
Hancock and Sahl, *Nat. Biotechnol.*, 24:1551-1557, 2006
Hayes and Wolf, *Biochem. J.*, 272:281-295, 1990.
Jacoby and Archer, *J. Med.*, 324:601-612, 1991.
Japelj et al., *J. Am. Chem. Soc.*, 129:1022-1023, 2007.
Kim et al., *Biochemistry*, 43:2373-2383, 2004.
Kirk et al., *J. Am. Chem. Soc.*, 122:980-981, 2000.
Kudyba et al., *Carb. Res.*, 342:499-519, 2007.
Kuhn et al., *Liebigs Ann. Chem.*, 611:236-241, 1958.
Liu et al., *Angew. Chem. Int. Ed.*, 43:1158-1162, 2004.
Magnet and Blanchard, *Chem. Rev.*, 105: 477-497, 2005.
Majerle et al., *J. Antimicrob. Chemother.*, 51:1159-1165, 2003.
Makovitzki et al., *Proc. Natl. Acad. Sci. USA*, 103:15997-16002, 2006.
Malina and Shai, *Biochem. J.*, 390:695-702, 2005.
Mei et al., *Bioorg. Med. Chem. Chem. Lett.*, 5:2755-2760, 1995.
Moazed and Noller, *Nature*, 327:389-394, 1987.
Moore et al., *Antimicrob. Agent. Chemother.*, 29:496-500, 1986.
Neu, *Science*, 257:1064-1073, 1992.
Ohyama et al., *Chem. Commun.*, 467-468, 1998.
Palermo and Kuroda, *Biomacromolecules*, 10:1416-1428, 2009.
Park et al., *Biochem. Biophys. Res. Commun.*, 244:253-257, 1998.
Patch and Barron, *J. Am. Chem. Soc.*, 48:3127-3129, 2004.
Peterson et al., *J. Bacteriol.*, 164:1256-1261, 1985.
Porter et al., *Nature*, 404:565, 2000.
Purohit and Stern, *Nature*, 370:659-662, 1994.
Quader et al., *J. Org. Chem.*, 72:1962-1979, 2007.
Radzishevsky et al., *Nat. Biotechnol.*, 25:657-659, 2007.
Remington's Pharmaceutical Sciences, 18th Ed., 1289-1329, Mack Printing Company, 1990.
Ribera et al., *J. Antimicrob. Chemother.*, 49:697-702, 2002.
Savage et al., *FEMS Microbiology Lett.*, 217:1-7, 2002.
Schmitt et al., *J. Am. Chem. Soc.*, 129:417-428, 2007.
Serrano et al., *Antimicrob. Agents. Chemother.*, 53:2215-2217, 2009.
Shai et al., *Curr. Protein Pept. Sci.*, 7:479-486, 2006.
Shakya and Wright, In: *Mechanisms of aminoglycoside antibiotic resistance in aminoglycoside antibiotics*, Arya (Ed.), Wiley, 119-140, 2007.
Shelburne et al., *Antimicrobial Agents Chemo.*, 48:4016-4019, 2004.
Smith and March's Advanced Organic Chemistry: Reactions, Mechanisms, and Structure (March's Advanced Organic Chemistry), 2001.
Som and Tew, *J. Phys. Chem. B.* 112:3495-3502, 2008.
Taber et al., *Microbiol. Rev.*, 429-457, 1987.
Tew et al., *Proc. Natl. Acad. Sci. USA*, 99:5110-5114, 2002.
Tran Ba Huy et al., *J. Clin. Invest.*, 77:1492-1500, 1986.
Vaara and Vaara, *Antimicrob. Agents. Chemother.*, 24:114-122, 1983.
Vaara, *Science*, 274: 939-940, 1996.
Vieira and Carmona-Ribeiro, *J. Antimicrobial Chemotherapy*, 58:760-767, 2006.
Von Ahsen and Noller, *Science*, 260:1500-1503, 1993.
Wakabayashi et al., *Antimicrob. Agents Chemother.*, 43:1267-1269, 1999.
Wang and Tor, *J. Am. Chem. Soc.*, 119:8734-8735, 1997.
Werstuck et al., *Chem. Biol.*, 3:129-137, 1996.
Wright et al., *Adv. Exp. Med. Biol.*, 456:27-69, 1998.
Zasloff, *Nature*, 415:389-395, 2002.
Zhanel et al., *Antimicrob. Agents. Chemother.*, 52:1430-1437, 2008.
Zhang et al., *J. Antibiot.*, 62:539-544, 2009.
Zhang et al., *J. Med. Chem.*, 51:7563-7573, 2008.
Zorko et al., *Antimicrob. Agents Chemother.*, 49:2307-2313, 2005.

The invention claimed is:

1. An aminoglycoside derivative of the following formula:

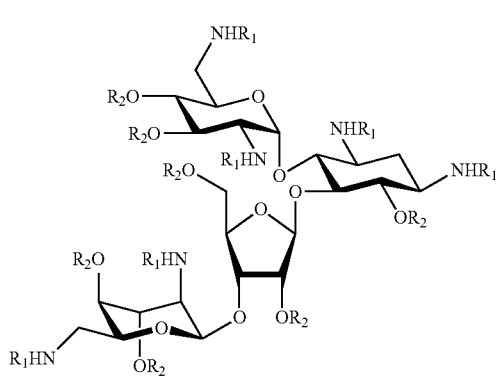

wherein each $R_1$ is H and each $R_2$ is:

$C(O)NHC_6H_5$, $C(O)NH$-p-$C_6H_4Cl$, $C(O)NHC_6H_{13}$, $C(O)NH$-p-$C_6H_4N(Me)_2$, $CH_2$-p-$C_6H_4Cl$, $CH_2$-p-$C_6H_4C(CH_3)_4$, or $CH_3$;

or pharmaceutically-acceptable salts thereof.

2. The aminoglycoside derivative of claim 1, wherein $R_2$ is $C(O)NHC_6H_5$.

3. A pharmaceutical composition comprising an aminoglycoside derivative of claim 1.

4. An aminoglycoside derivative of the following formula:

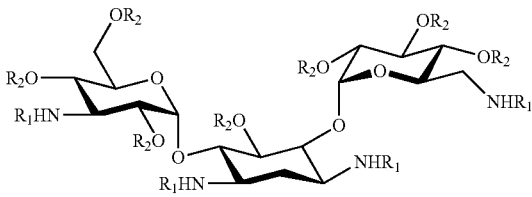

wherein each $R_1$ is H and each $R_2$ is:

$C(O)NHC_6H_5$, $C(O)NHC_6H_{13}$, $C(O)NH$-p-$C_6H_4N(Me)_2$, $CH_2C_6H_5$, $CH_2$-p-$C_6H_4Cl$, or $CH_3$;

or pharmaceutically-acceptable salts thereof.

5. A pharmaceutical composition comprising an aminoglycoside derivative of claim 4.

6. An aminoglycoside derivative of the following formula:

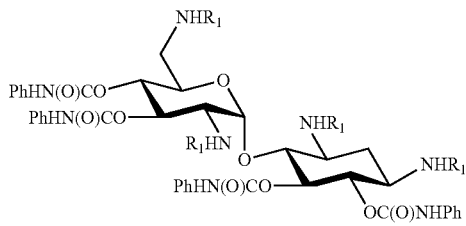

wherein each $R_1$ is H, $C(NH)NH_2$, $C(O)(NH_2)$, alkyl$_{(C\leq18)}$, substituted alkyl$_{(C\leq18)}$, alkenyl$_{(C\leq18)}$, substituted alkenyl$_{(C\leq18)}$, alkynyl$_{(C\leq18)}$, substituted alkynyl$_{(C\leq18)}$, aryl$_{(C\leq18)}$, substituted aryl$_{(C\leq18)}$, aralkyl$_{(C\leq18)}$, substituted aralkyl$_{(C\leq18)}$, heteroaryl$_{(C\leq18)}$, substituted heteroaryl$_{(C\leq18)}$, heteroaralkyl$_{(C\leq18)}$, substituted heteroaralkyl$_{(C\leq18)}$, acyl$_{(C\leq18)}$, substituted acyl$_{(C\leq18)}$;

or pharmaceutically-acceptable salts thereof.

7. The aminoglycoside derivative of claim 6, wherein $R_1$ is H.

8. An aminoglycoside derivative of the following formula:

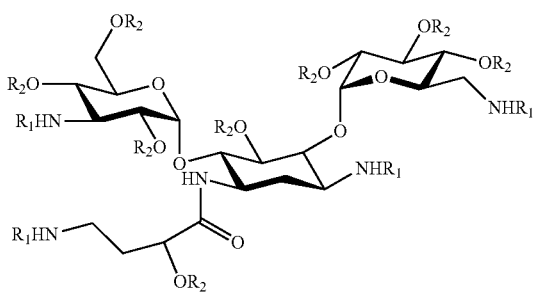

wherein each $R_1$ and each $R_2$ are each independently:

H, $C(NH)NH_2$, $C(O)(NH_2)$, alkyl$_{(C\leq18)}$, substituted alkyl$_{(C\leq18)}$, alkenyl$_{(C\leq18)}$, substituted alkenyl$_{(C\leq18)}$, alkynyl$_{(C\leq18)}$, substituted alkynyl$_{(C\leq18)}$, aryl$_{(C\leq18)}$, substituted aryl$_{(C\leq18)}$, aralkyl$_{(C\leq18)}$, substituted aralkyl$_{(C\leq18)}$, heteroaryl$_{(C\leq18)}$, substituted heteroaryl$_{(C\leq18)}$, heteroaralkyl$_{(C\leq18)}$, substituted heteroaralkyl$_{(C\leq18)}$, acyl$_{(C\leq18)}$, substituted acyl$_{(C\leq18)}$, provided that not all $R_1$ and $R_2$ are H;

or pharmaceutically-acceptable salts thereof.

9. The aminoglycoside derivative of claim 8, wherein $R_1$ is H; and $R_2$ is $C(O)NHC_6H_5$, $C(O)NHC_6H_{13}$, $CH_2C_6H_5$, $CH_2$-p-$C_6H_4Cl$, or $CH_3$.

10. The aminoglycoside derivative of claim 9, wherein $R_2$ is $C(O)NHC_6H_{13}$.

11. A pharmaceutical composition comprising an aminoglycoside derivative of claim 8.

* * * * *